US007091030B2

(12) United States Patent
Setiawan et al.

(10) Patent No.: US 7,091,030 B2
(45) Date of Patent: Aug. 15, 2006

(54) COMPOSITION FOR THE PRESERVATION OF VIRUSES

(76) Inventors: Kerrie Setiawan, 14 Moorhen Place, Wynn Vale, South Australia, 5127 (AU); Fiona Helen Cameron, 28 Chelmsford Avenue, Lindfield, New South Wales, 2070 (AU)

(*) Notice: Subject to any disclaimer, the term of this patent is extended or adjusted under 35 U.S.C. 154(b) by 406 days.

(21) Appl. No.: 10/317,171

(22) Filed: Dec. 12, 2002

(65) Prior Publication Data

US 2004/0038410 A1 Feb. 26, 2004

(30) Foreign Application Priority Data

Dec. 12, 2001 (AU) .................................... PR9449
Feb. 14, 2002 (AU) .................................... PS0545

(51) Int. Cl.
*C12N 7/00* (2006.01)
*C12N 7/01* (2006.01)
*A61K 31/20* (2006.01)

(52) U.S. Cl. ................... 435/235.1; 424/93.6; 514/558

(58) Field of Classification Search ..................... None
See application file for complete search history.

(56) References Cited

U.S. PATENT DOCUMENTS

| | | | |
|---|---|---|---|
| 4,357,324 A | 11/1982 | Montgomery et al. | |
| 5,122,458 A | 6/1992 | Post et al. | |
| 5,561,062 A | 10/1996 | Varanelli et al. | |
| 5,854,224 A | 12/1998 | Lockett et al. | |
| 5,866,551 A | 2/1999 | Benoit et al. | |
| 5,885,590 A | 3/1999 | Hunter et al. | |
| 5,906,922 A | 5/1999 | Whittaker et al. | |
| 6,017,896 A | 1/2000 | Sorscher et al. | |
| 6,022,530 A | 2/2000 | Gers-Barlag et al. | |
| 6,033,885 A | 3/2000 | Latta et al. | |
| 6,066,624 A | 5/2000 | Woo et al. | |
| 6,083,720 A | 7/2000 | Chroboczek et al. | |
| 6,113,913 A | 9/2000 | Brough et al. | |
| 6,124,270 A * | 9/2000 | Haensler | 514/44 |
| 6,165,779 A * | 12/2000 | Engler et al. | 435/320.1 |
| 6,218,180 B1 | 4/2001 | Kurtzman et al. | |
| 6,225,289 B1 * | 5/2001 | Kovesdi et al. | 514/23 |
| 6,749,863 B1 * | 6/2004 | Chang et al. | 424/450 |
| 2002/0045249 A1 | 4/2002 | Both et al. | |

FOREIGN PATENT DOCUMENTS

| | | |
|---|---|---|
| EP | 0 173 552 A1 | 3/1986 |
| EP | 0 415 731 A2 | 3/1991 |
| EP | 1 179 349 A1 | 2/2002 |
| FR | 2 651 793 | 3/1991 |
| JP | 9-234069 | 9/1997 |
| WO | WO94/03594 A1 | 2/1994 |
| WO | WO94/19478 A1 | 9/1994 |
| WO | WO94/21792 A2 | 9/1994 |
| WO | WO94/26914 A1 | 11/1994 |
| WO | WO95/05835 A1 | 3/1995 |
| WO | WO95/07718 A2 | 3/1995 |
| WO | WO95/14091 A2 | 5/1995 |
| WO | WO95/19434 A1 | 7/1995 |
| WO | WO96/03508 A1 | 2/1996 |
| WO | WO96/05218 A1 | 2/1996 |
| WO | WO96/25506 A1 | 8/1996 |
| WO | WO97/01358 A1 | 1/1997 |
| WO | WO97/06826 A1 | 2/1997 |
| WO | WO97/25339 A1 | 7/1997 |
| WO | WO98/00524 A1 | 1/1998 |
| WO | WO98/02522 A1 | 1/1998 |
| WO | WO98/22144 A2 | 5/1998 |
| WO | WO99/27073 A1 | 6/1999 |
| WO | WO99/29710 A2 | 6/1999 |
| WO | WO99/39740 A2 | 8/1999 |
| WO | WO99/41416 A2 | 8/1999 |
| WO | WO99/46385 A2 | 9/1999 |
| WO | WO99/58156 A1 | 11/1999 |
| WO | WO00/01418 A1 | 1/2000 |
| WO | WO00/29024 A1 | 5/2000 |
| WO | WO00/30687 A1 | 6/2000 |
| WO | WO00/32233 A2 | 6/2000 |
| WO | WO00/32754 A1 | 6/2000 |
| WO | WO00/34444 A2 | 6/2000 |
| WO | WO00/49147 A1 | 8/2000 |
| WO | WO00/52156 A1 | 9/2000 |
| WO | WO00/61141 A2 | 10/2000 |
| WO | WO00/61605 A1 | 10/2000 |
| WO | WO00/62815 A2 | 10/2000 |
| WO | WO00/74723 A2 | 12/2000 |
| WO | WO01/11066 A1 | 2/2001 |
| WO | WO01/21217 A2 | 3/2001 |
| WO | WO02/053183 A1 | 7/2002 |

OTHER PUBLICATIONS

Chillon M et al. 1998. Adenovirus complexed with polyethylene glycol and cationic lipid is shielded from neutralizing antibodies in vitro. Gene Therapy 5: 995-1002.*

Fasbender A et al. 1997. Complexes of adenovirus with polycationic polymers and cationic lipids increase the efficiency of gene transfer in vitro and in vivo. J Biol Chem 272: 6479-6489.*

Croyle, MA et al., Pharm Dev and Technol., vol. 3, 1998, pp. 373-383.

Liu, F. et al., Pharm Res., vol. 13, 1996, pp. 1856-1860.

Allison, SD et al., Arch Biochem Biophys., vol. 365, 1999, pp. 289-298.

Sudhanshu Vrati et al., Virology, vol. 220, 1996, pp. 200-203.

Linda J. Lockett et al., Virology, vol. 294, 2002, pp. 333-341.

(Continued)

*Primary Examiner*—Irene Marx
*Assistant Examiner*—Lora E Barnhart
(74) *Attorney, Agent, or Firm*—Birch, Stewart, Kolasch & Birch, LLP

(57) ABSTRACT

This invention relates to a composition for the preservation of a virus, the composition including a virus, a lipid and a cryoprotectant.

55 Claims, 7 Drawing Sheets

OTHER PUBLICATIONS

D. Voeks et al., Gene Therapy, vol. 9, 2002, pp. 759-768.
Rosetta Martiniello-Wilks et al., Cancer Gene Therapy, vol. 9, 2002, pp. 443-452.
S. Dean Allison et al., Journal of Pharmaceutical Sciences, vol. 89, No. 5, May 2000, pp. 682-691.
T. Arakawa et al., Biochemistry, vol. 21, No. 25, 1982, pp. 6331-6618.
Michael W. Townsend et al., Journal of Parenteral Science and Technology, vol. 42, 1988, pp. 190-199.
Thomas M. Foster et al., International Journal of Pharmaceutics, vol. 134, 1996, pp. 193-201.
Sudhanshu Vrati et al., Virology, vol. 209, pp. 400-408, 1996.
Michael Petukhov et al., Protein Science, vol. 8, 1999, pp. 1982-1989.
Arno T. P. Skrabanja et al., PDA J. Pharm. Sci. Technol., vol. 48, No. 6, 1994, pp. 311-317.
Thomas Osterberg et al., Pharmaceutical Research, vol. 14, No. 7, 1997, pp. 892-898.
Henry R. Costantino et al., Journal of Pharmaceutical Sciences, vol. 87, No. 11, Nov. 1998, pp. 1412-1420.
Fiona H. Cameron et al., Bioch. Biophys. Acta, vol. 1417, 1999, pp. 37-50.
T. Lockett et al., Clinical and Exper. Pharm. and Phys., vol. 27, 2000, pp. 563-567.
DJ Voeks et al., Biotechniques, Jul. 2001, vol. 31, No. 1, pp. 46-49.
Lotte Kreilgaard et al., Journal of Pharmaceutical Sciences, vol. 88, No. 3, Mar. 1999, pp. 281-290.
Kunihiko Gekko et al., Biochemistry, vol. 20, 1981, pp. 4667-4676.
Harry Levine et al., Cryo-Letters, vol. 9, 1988, pp. 21-63.
Manohar Katakam et al., Journal of Pharmaceutical Sciences, vol. 84, No. 6, Jun. 1995, pp. 713-716.
Attar S. Chawla et al., Diabetes, vol. 34, 1985, pp. 420-424.
Kunio Takeda et al., Biochem. Biophys. Acta., vol. 957, 1988, pp. 340-344.
Jeffrey L. Cleland et al., Crit. Rev. Ther. Drug Carrier Syst., vol. 10, 1993, pp. 307-377.
G. Gonzalez et al., J. Colloid Interface Sci., vol. 32, 1970, pp. 55-61.
Pao-Li Wang et al., J. Parenter Sci. Technol., vol. 47, 1993, pp. 183-189.
Mark C. Manning et al., Pharmaceutical Research, vol. 6, No. 11, 1989, pp. 903-918.
Alexander V. Vologodskii et al., Annu. Rev. Biophys. Biomol. Struct., vol. 213, 1994, pp. 609-643.
Sergio Simoes et al., Current Opinion in Molecular Therapeutics, vol. 1, 1999, pp. 147-157.
T. Yamamoto, Can. J. Microbiol., vol. 13, 1967, pp. 1139-1149.
P. L. Stewart et al., pp. 25-38, 1995.
Thomas J. Anchordoquy et al., Journal of Pharmaceutical Sciences, vol. 87, No. 9, Sep. 1998, pp. 1046-1051.
Thomas J. Anchordoquy et al., Archives of Biochemistry and Biophysics, vol. 348, No. 1, Dec. 1, 1997, pp. 199-0206.
Bei Li et al., Journal of Pharm. Sciences, vol. 89, No. 3, Mar. 2000, pp. 355-364.
Feng Liu et al., Pharm. Research, vol. 13, No. 12, 1996, pp. 1856-1860.
Michael J. Pikal et al, BioPharm, vol. 3, Oct. 1990, pp. 26-30.

* cited by examiner

COMPOSITION FOR THE PRESERVATION OF VIRUSES

This nonprovisional application claims priority under 35 U.S.C. § 119(a) on Patent Application No. PR9449 filed in Australia on Dec. 12, 2001 and PS0545 filed in Australia on Feb. 14, 2002, which is herein incorporated by reference.

FIELD OF THE INVENTION

The present invention relates to compositions for the preservation of viruses. The present invention also relates to methods for preparing compositions for the preservation of viruses.

It will become apparent from the following description that the viral compositions according to the present invention are most likely to be pharmaceutical compositions for the purposes of the delivery of viral particles for gene therapy or vaccination. However, it must be appreciated that the invention is not to be limited in its application to only pharmaceutical compositions.

BACKGROUND OF THE INVENTION

Gene therapy broadly refers to the transfer of genetic material into cells and the expression of that material in those cells for a therapeutic purpose. The goal is to produce the desired protein in the appropriate quantity and the proper location. Although a variety of methods have been developed to deliver therapeutic nucleic acids to cells, many of these methods are limited by relatively inefficient transfer of the therapeutic nucleic acid to the target cells. Because viruses are highly efficient at infecting susceptible cells, viruses are now recognised as being useful vehicles for the transfer of therapeutic nucleic acids into cells for the purpose of gene therapy.

Viruses fall broadly into two distinct groups: those that integrate into the genome of transduced cells and those that do not. An integrating virus inserts its viral genome into host DNA to facilitate long-term gene expression. For a non-integrating virus, however, the viral genome exists extra-chromosomally as an episome in the nucleus of transduced cells. Depending on the ability of the virus to replicate, the viral genome is either passed on faithfully to every daughter cell or is eventually lost during cell division.

Retroviruses and adeno-associated viruses (AAVs) may integrate into the host DNA to provide a steady level of expression following transduction and incorporation into the host genome. As the target DNA is replicated, so too is the inserted therapeutic gene embedded in the transferred chromosomal DNA. Thus, transduction via these vectors can produce durable gene expression. This can be advantageous in tumour vaccine strategies in which a steady level of gene expression may enhance efficacy.

In contrast, adenovirus and vaccinia virus vectors do not integrate into the host DNA but exist as episomes. Thus, a transferred gene is expressed without actual integration of the gene into the target cell genome. Generally, non-integrating viruses are used when transient gene expression is desired.

Examples of viruses that may be used to deliver nucleic acids to cells for gene therapy purposes include adenovirus, adeno-associated virus (AAV), retrovirus, herpes simplex virus, vaccinia virus, poliovirus, sindbis virus, HIV-1, avian leukosis virus, sarcoma virus, Epstein-Barr virus, papillomavirus, foamy virus, influenza virus, Newcastle disease virus, sendai virus, lymphocytic choriomeningitis virus, polyoma virus, reticuloendotheliosis virus, Theiler's virus, and other types of RNA and DNA viruses.

The use of attenuated and killed viruses for purposes of vaccination is also well known. In addition, viruses are also becoming increasingly important as tools for research and diagnostics. The increasing importance of viruses as tools for gene therapy, vaccination, and research and diagnosis has led to a need to develop viral compositions that may be manufactured, stored and used without compromising viral efficacy. For example, viral compositions for vaccination must be able to maintain the immunogenicity of a virus, or the immunogenicity of a component of the virus. In the case of compositions of viruses to be used for gene therapy, it is critical that the efficacy of the live viral formulations carrying therapeutic transgenes be maintained.

Because viruses are biological entities consisting of a nucleic acid encapsulated by a protein coat, they are susceptible to the same chemical and physical processes that may degrade or inactivate proteins and nucleic acids. In particular, live viruses may often be very susceptible to damage, as any change in the conformation or integrity of one or more components of the virus coat or the encapsulated nucleic acid may lead to a loss of infectivity. As such, biopharmaceutical products containing compositions of viruses for vaccination or gene therapy usually require stringent conditions to avoid physicochemical degradation and to maintain biological activity. Degradation of viruses in such compositions may occur during isolation, production, purification, formulation, storage, shipping or delivery of the virus. Accordingly, biopharmaceutical compositions of viruses must be formulated to provide protection of the virus against factors such as temperature, pH, pressure, oxidising agents, ionic content, light, radiation, ultrasound, and changes in phase (for example as occurs during freezing and thawing ("freeze-thawing").

In addition to the factors already discussed, other factors such as viral concentration, the size and structure of the encapsulated nucleic acid, container composition, headspace gas, and number of freeze-thaw cycles may all affect the activity of viral compositions.

As a consequence, the utility of many viruses in biopharmaceutical preparations is often limited by the instability of compositions of the viruses, particularly upon storage. For example, even when viral compositions are stored at very low temperature (for example −80° C.) in the frozen state, a significant loss of infectivity may still occur over time. A further loss of infectivity may occur upon thawing of the frozen viral composition.

In addition, as low temperature storage conditions are not always available, it would be advantageous to develop formulations that improve the preservation of frozen viral formulations above −80° C. for extended periods of time, such as extended storage at temperatures just below freezing. Indeed, viral compositions that must be stored at very low temperature and cannot be stored at standard freezer temperatures (for example −10° C. to −20° C.) for substantial periods of time represent a serious impediment to the widespread clinical use of many viruses.

As will be also appreciated, the storage of products at standard freezer temperatures may also be problematic, because often such freezers undergo temperature cycling that may result in the viral composition being subjected to temperatures above freezing, and as such the compositions may undergo repeated cycles of freezing and thawing. Freeze-thawing may also occur during large scale production, handling or distribution.

It would also be advantageous to develop viral compositions that can maintain the desired pH of the composition for extended periods of time despite being exposed to refrigeration temperatures and/or subjected to conditions such as freeze-thawing, especially the slow rate of freeze-thawing that may occur during large scale production, handling or distribution.

Finally, increasingly high concentrations of virus are also being required for therapeutic purposes. However, the concentration of virus in a composition may present additional problems to the ability to preserve a virus. In particular, a high concentration of virus may contribute significantly to viral instability due to aggregation and/or precipitation.

Therefore for many viruses a deficiency has been the inability to formulate compositions that acceptably preserve the virus, particularly in the frozen state. Such deficiencies with the ability to preserve the activity of viral compositions often preclude their use for gene therapy, for vaccination, or for other purposes.

It is therefore an aim of the present invention to provide a composition for the improved preservation of viruses.

Throughout this specification reference may be made to documents for the purpose of describing various aspects of the invention. However, no admission is made that any reference cited in this specification constitutes prior art. In particular, it will be understood that the reference to any document herein does not constitute an admission that any of these documents forms part of the common general knowledge in the art in Australia or in any other country. The discussion of the references states what their authors assert, and the applicant reserves the right to challenge the accuracy and pertinency of any of the documents cited herein.

SUMMARY OF THE INVENTION

The present invention provides a composition for the preservation of a virus, the composition including a virus, a lipid and a cryoprotectant.

The present invention further provides a method of producing a composition for the preservation of a virus, the method including the step of preparing a liquid composition including a virus, a lipid and a cryoprotectant.

In the context of the present invention, it has been determined that the activity of a virus in a composition may be preserved by including in the composition a lipid and a cryoprotectant.

The composition according to the present invention provides for improved preservation of a virus. For example, the composition provides for improved storage of a virus upon storage. The composition also provides for improved preservation of a virus upon freezing and provides for improved preservation of the virus upon storage of the composition in the frozen state. The composition further provides for improved preservation of a virus upon thawing. The improved preservation of the virus in the composition is also evident over a broad range of storage temperatures and storage periods, and over multiple cycles of freezing and thawing ("freeze-thawing").

It is to be understood that while the composition according to the present invention may be used for the preservation of viable virus particles, the composition according to the present invention may also be used for the improved preservation of attenuated virus particles, killed virus particles, non-viable viral particles, synthetic viruses, or one or more constituents of viable, killed, non-viable or synthetic viruses.

It will also be appreciated that not only may the present invention be used for pharmaceutical compositions for medical applications, such as the delivery of virus for the purposes of gene therapy or the delivery of viruses or viral constituents for vaccination, the present invention may also be used for compositions for the preservation of viable, attenuated, killed, non-viable and synthetic viral particles for non-medical applications, such as the preservation of viral preparations for research and diagnostic applications.

Various terms that will be used throughout this specification have meanings that will be well understood by a skilled addressee. However, for ease of reference, some of these terms will now be defined.

The term "preservation" as used throughout the specification is to be understood to mean that a desired activity of a virus (such as infectivity, transduction or immunogenicity) does not decrease substantially over a given period of time, or that a desired activity of a virus does not decrease substantially after a particular treatment. For example (i) the activity of a virus in a composition according to the present invention may not decrease substantially when the virus is stored in a frozen composition for a given period of time; and/or (ii) the activity of the virus in a composition according to the present invention may not substantially decrease when the composition is freeze-thawed, or subjected to repeated cycles of freeze-thawing.

In the context of the present invention, the ability of a composition to preserve a virus is to be understood to be improved over similar compositions that do not contain a lipid, or compositions that do not contain a cryoprotectant. Accordingly, the composition according to the present invention will show an activity of the virus over a given period of time, or will show an activity of the virus after a particular treatment (eg freeze-thawing), that is higher than a similar composition that does not contain a lipid, or a similar composition that does not contain cryoprotectant.

In this regard, the demonstration of the preservation of a virus in a composition according to the present invention will be achieved by a suitable biological assay. As will be appreciated, given the degree of variability in biological systems, in determining the ability of a composition to preserve a virus, sufficient repetitions of any biological assay will need to be performed to statistically demonstrate that the composition is able to preserve the virus.

The term "virus" as used throughout the specification is to be understood to mean any natural, recombinant, in vitro packaged or synthetic virus.

The term "viral composition" as used throughout the specification is to be understood to mean any composition that may be used for the preservation of a virus (or a part of a virus) for therapeutic purposes, or for the preservation of virus (or part of a virus) generally. The term not only encompasses the composition according to the present invention, but also encompasses the composition according to the present invention with other any other additives, such as excipients.

The term "lipid" as used throughout the specification is to be understood to mean any fatty acid and derivatives of fatty acids, glycerol-derived lipids including phospholipids, sphingosine-derived lipid (including ceramides, cerebrosides, gangliosides and sphingomyelins) and glycolipids, terpenes and their derivatives, long chain alcohols and waxes. In referring to such lipids, it will be appreciated that these molecules are amphiphilic and will contain a substantially hydrophilic moiety coupled to a substantially hydrophobic moiety. The hydrophilic moiety will contain one or more substantially hydrophilic groups, and the hydrophobic moiety will contain one or more substantially hydrophobic groups.

The term "cryoprotectant" as used throughout the specification is to be understood to mean any molecule that has the function of substantially inhibiting the formation of ice crystals upon freezing of a liquid composition. In this regard, it will be understood that a molecule with cryoprotective function may also perform one or more additional functions in any particular composition (for example being a tonicity modifier or lyoprotectant). Accordingly, the demonstration that a molecule has a cryoprotectant capacity will be achieved by a suitable method known in the art to test whether the molecule has the ability to inhibit the formation of crystals upon the freezing of a liquid composition.

The term "surfactant" as used throughout the specification is to be understood to mean any compound that can reduce the interfacial tension between two immiscible phases. In this regard, it will be understood that a molecule with surfactant function may also perform one or more additional functions in any particular composition. Accordingly, the demonstration that a molecule has a surfactant capacity will be achieved by a suitable method known in the art to test whether the molecule has the ability to reduce the interfacial tension between two immiscible phases.

GENERAL DESCRIPTION OF THE INVENTION

Figure 1:
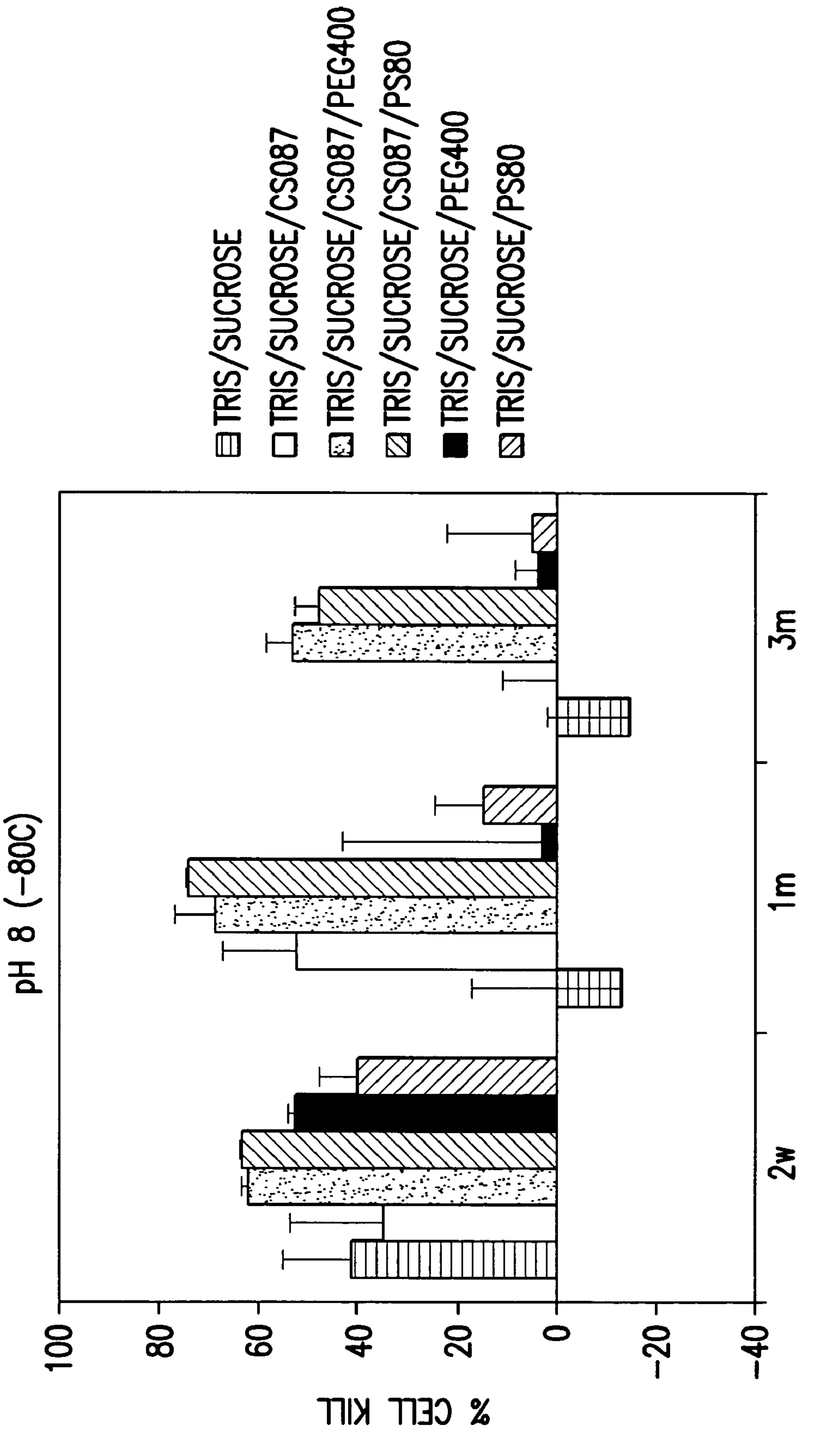
FIG. 1: shows the storage stability of various viral compositions at pH8 and −80° C.

As mentioned above, the composition of the present invention provides for the improved preservation of virus particles. Preferably, the virus particles are selected from one or more of the group consisting of Adenoviridae including Mastadenovirus such as Human Adenovirus and Atadenovirus such as Ovine Adenovirus; Herpesviridae; Poxviridae including vaccinia, fowlpox, swinepox and sheeppox; Papovaviridae; Orthohepadnavirus; Parvoviridae including adeno-associated virus; Birnaviridae; Reoviridae; Flaviviridae; Picornaviridae including poliovirus; Togaviridae including Sindbis virus and Semliki Forest virus; Filoviridae; Paramyxoviridae; Rhabdoviridae; Arenaviridae; Bunyaviridae; Orthomyxoviridae; Retroviridae including Lentivirus. More preferably, the virus particle is derived from the Adenoviridae family of viruses.

More preferably, the virus is an Atadenovirus. Most preferably, the virus is an ovine atadenovirus.

For the purposes of the various forms of the present invention, the virus is preferably a recombinant virus. More preferably, the virus is a recombinant virus that has utility for the purposes of gene therapy. In a particularly preferred embodiment, the virus is a recombinant ovine adenovirus, such as the adenoviral vector OAdV623 or derivatives of this vector. OAdV623 encodes the purine nucleoside phosphorylase (PNP) gene which catalyses the conversion of the immunosuppressive prodrug Fludarabine to the toxic 2-fluoro-adenine product. Adenoviral vector OAdV623 is as described in Lockett L. J. and Both G. W. (2002) *Virology* 294:333–341.

The composition according to the present invention may be used for the preservation of viral particles that retain the ability to infect or transduce cells, or for the preservation of viral particles that have been attenuated, killed, are non-viable, have been produced by in vitro packaging or are of synthetic origin. The composition according to the present invention may also be used for the preservation of parts of a virus, such as the preservation of one or more constituents of the virus coat. Preferably, the viral particles are viable viral particles.

In this regard, an attenuated virus is to be understood to mean a virus whose virulence has been lowered by a biological, physical or chemical process. For example, the virulence of a virus may be attenuated by passaging through a semi-permissive host.

A killed virus is to be understood to mean a viral particle that has been inactivated by a treatment so that the viral particle no longer retains the ability to infect a permissive host. Examples of treatments that may kill a viral particle are heat or chemical modification.

A non-viable virus is to be understood to mean a viral particle that is not able to infect or transduce permissive host cells.

A synthetic virus is to be understood to mean any nucleic acid packaged with a protein and/or lipid coat.

The composition according to the present invention may be used for the preservation of viruses that are to be used for medical applications. Preferably, the composition is for the preservation of viruses that are to be used for the purposes of gene therapy. More preferably, the composition is for the preservation of viruses that are to be used for the delivery of therapeutic nucleic acids to prostatic cells for gene therapy.

The composition according to the present invention may also be used for the preservation of viruses that are to be used for the purposes of eliciting an immunogenic response, such as for vaccination. It will be understood in this regard that the composition may be used for the preservation of whole viruses, or for the preservation of one or more immunogenic constituents of a virus, such as the preservation of one or more polypeptides that make up part of the virus coat.

When the composition according to the present invention is used for the preservation of a virus to be used for medical applications, the composition may also include one or more pharmaceutically acceptable additives, such as pharmaceutically acceptable salts, amino acids, polypeptides, polymers, solvents, buffers and bulking agents.

The composition according to the present invention is preferably a liquid composition. The liquid composition may be a substantially aqueous composition or a composition composed of one or more other solvents. Most preferably, the composition is a substantially aqueous composition.

The composition may be stored in a container suitable for the preservation of the virus, such as borosilicate glass. The composition may also be stored under a gaseous atmosphere that is suitable for the preservation of the virus including air, argon or nitrogen.

The composition according to the present invention may also be used for the preservation of viable, attenuated, killed, non-viable or synthetic viruses for research applications. For example, the composition may be used for the preservation of viral particles that have use in research applications, such as the use of viral preparations for immunological research. The composition may also be used for the preservation of viral preparations for use in molecular biological research, such as the use of viral preparations for the infection or transduction of cells in culture.

In a similar fashion, the composition according to the present invention may also be used for the preservation of viral particles that have use in diagnostic applications, such as the use of viral preparations as positive and negative test standards for diagnostic applications.

With regard to viral activity, the activity of the virus may be measured by any suitable assay that is known in the art. Such assays include both direct and indirect biological and physicochemical assays of viral activity. Examples of direct assays include the measurement of the number of infectious viral particles in the product, the expression of a reporter gene or other transgene carried by the virus, the cell killing or cell viability following viral infection or transduction of a suitable cell line, or the quantity of components produced following administration of the viral particles or constituents to a suitable model (eg. immune response in case of vaccination). Examples of indirect assays include the measurement of the number of intact and non-aggregated viral particles or the size of the viral particles (as an indication of viral aggregation) in the product.

For example, for determining the activity of viable viral particles, the number of permissive cells killed following infection or transduction with a defined amount of virus may be determined by any suitable assay. Alternatively, as an indirect measure of viral activity, the number of intact and non-aggregated viral particles in the product may be determined by anion-exchange HPLC and the particle size determined by light scattering analysis.

The concentration of virus in the composition of the present invention may also affect the ability of the composition to preserve the virus. Preferably, the concentration of virus in the composition is in the range from $1\times10^6$ to $1\times10^{14}$ virus particles/ml. More preferably, the concentration of virus is in the range from $1\times10^8$ to $5\times10^{12}$ virus particles/ml.

The lipid in the composition according to the present invention is any fatty acid or derivative of a fatty acid, glycerol-derived lipid including a phospholipid, sphingosine-derived lipid (including ceramides, cerebrosides, gangliosides and sphingomyelins) and glycolipid, terpene and their derivatives, long chain alcohol and wax. The lipid is an amphiphilic molecule that contains a substantially hydrophilic moiety coupled (directly or by way of a spacer) to a substantially hydrophobic moiety. The hydrophilic moiety will contain one or more substantially hydrophilic groups and the hydrophobic moiety will contain one or more substantially hydrophobic groups.

The lipid present in the composition according to the various forms of the present invention may be a cationic lipid, anionic lipid, zwitterionic lipid, non-ionic lipid or any combination of such lipids.

Examples of cationic lipids include 2,3-dioleyloxy-N-[2 (sperminecarboxamido)ethyl]-N,N-dimethyl-1-propanaminium trifluoroacetate (DOSPA), dioctadecylaminoglycyl spermine (DOGS), dipalmitoyl phosphatidylethanolamyl spermine (DPPES), 1,3-dioleoyoxy-2-(6-carboxy-spermyl)-propylamide (DOSPER), dioleyldimethylammonium chloride (DODAC), N-[1-(2,3-dioleyloxy)propyl]-N,N,N-trimetylammonium chloride (DOTMA), 1,2-dioleoyl-sn-glycero-3-trimethylammonium-propane (DOTAP), 1,2-dimyristyloxypropyl-3-dimethyl-hydroxy ethyl ammonium bromide (DMRIE), 3β-(N-((N', N'-dimethylamino)ethane) carbamoyl)-cholesterol (DC-Chol), dimethyldioctadecyl ammonium bromide (DDAB), 1-[2-(oleoyoxy)-ethyl]-2-oleyl-3-(2-hydroxyethyl)imidazolinium chloride (DOTIM), bis(oleoyl)-trimethylaminomethylphosphonate, 1,2-dimyristoylglycerolpentalysine salt, N,N',N'',N'''-tetramethyl-N,N',N'',N'''-tetrapalmitylspermine (TMTPS), cetyltrimethylammonium bromide (CTAB) and the following proprietary cationic lipids: Lipofectamine (DOSPA:DOPE 3:1 w/w), Lipofectin (DOTMA:DOPE 1:1 w/w), Lipofectace (DDAB:DOPE 1:1.25 w/w), Transfectam, Cellfectin (TMTPS:DOPE 1:1.5 M/M), Superfect, LipoTaxi, DMRIE-C (DMRIE/cholesterol: 1:1) and trilysine-carpryloyl-tris-trilaurate (T-shape; CS087).

Examples of anionic lipids include 1,2-dioleoyl-sn-glycero-3-[phospho-L-serine] (DOPS), 1,2-dimyristoyl-sn-glycero-3-phosphoglycerol (DMPG), and PEG-PE lipids such as 1,2-dimyristoyl-sn-glycero-3-phosphoethanolamine-N-[poly(ethyleneglycol) 2000] (PEG2000 DMPE), 1,2-dipalmitoyl-sn-glycero-3-phosphoethanolamine-N-[poly(ethyleneglycol) 2000] (PEG2000 DPPE), 1,2-distearoyl-sn-glycero-3-phosphoethanolamine-N-[poly(ethyleneglycol) 2000] (PEG2000 DSPE).

Examples of zwitterionic/neutral lipids include 1,2-dioleoyl-sn-glycero-3-phosphoethanolamine (DOPE), 1,2-dioleoyl-sn-glycero-3-phosphocholine (DOPC), 1,2-dimyristoyl-sn-glycero-3-phosphocholine (DMPC) and 1,2-dimyristoyl-sn-glycero-3-phosphoethanolamine (DM PE).

Preferably the lipid is a cationic lipid. More preferably, the lipid is a cationic lipid that has a hydrophilic moiety that includes one or more amino residues. More preferably, the lipid is a cationic lipid that has a hydrophilic moiety that includes one or more groups derived from amino acids. More preferably, the lipid is a cationic lipid that has a hydrophilic moiety that includes one or more groups derived from a positively charged amino acid, such as lysine, arginine or histidine. Most preferably, the lipid is a cationic lipid that has a hydrophilic moiety including one or more lysine groups.

In a particularly preferred embodiment, the lipid is a poly-cationic lipid. Preferably, the lipid is a poly-cationic lipid that has a hydrophilic moiety that includes two or more amino residues. More preferably, the lipid is a poly-cationic lipid that has a hydrophilic moiety that includes two or more groups derived from amino acids. More preferably, the lipid is a poly-cationic lipid that has a hydrophilic moiety that includes two or more groups derived from positively charged amino acids, such as lysine, arginine or histidine. Most preferably, the lipid is a poly-cationic lipid that has a hydrophilic moiety that includes three lysine groups.

The hydrophobic moiety of the lipid in the composition according to the present invention includes one or more hydrophobic groups. Hydrophobic groups include, but are not restricted to, acyl, alkyl, or alkoxy chains. Preferably, the one or more hydrophobic groups are derived from an acyl group of a fatty acid. More preferably, the one or more acyl groups have a carbon chain length of 3 to 24 carbon atoms. Most preferably, the one or more acyl groups is a laurate group.

Preferably, the lipid in the composition according to the present invention has a hydrophobic moiety that includes two or more hydrophobic groups. More preferably the lipid has a hydrophobic moiety that includes three hydrophobic groups. Most preferably, the lipid has a hydrophobic moiety that includes three laurate groups.

The lipid in the composition according to the present invention may also include a spacer group between the hydrophilic moiety and the hydrophobic moiety. The spacer group may include any combination or series of atoms that covalently join the hydrophilic and hydrophobic moieties. Preferably, the spacer region has a chain length equivalent to 1 to 30 carbon-carbon single covalent bonds.

In a preferred embodiment, the lipid in the composition according to the various forms of the present invention is derived from a tris-conjugated cationic lipid (or a salt thereof) according to the following general formula:

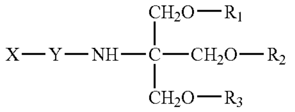

In this general formula, X represents the hydrophilic moiety, Y represents a spacer group (which may or may not be present), and $R_1$, $R_2$ and $R_3$ are acyl groups of fatty acids. Preferably, a spacer group Y is present in the molecule. Most preferably the spacer group has a chain length equivalent to 1 to 30 carbon-carbon single covalent bonds.

Most preferably, the lipid in the composition according to the various forms of the present invention is the molecule trilysine-carpryloyl-tris-trilaurate (T-shape; CS087), or a salt thereof, the structure of which is as follows:

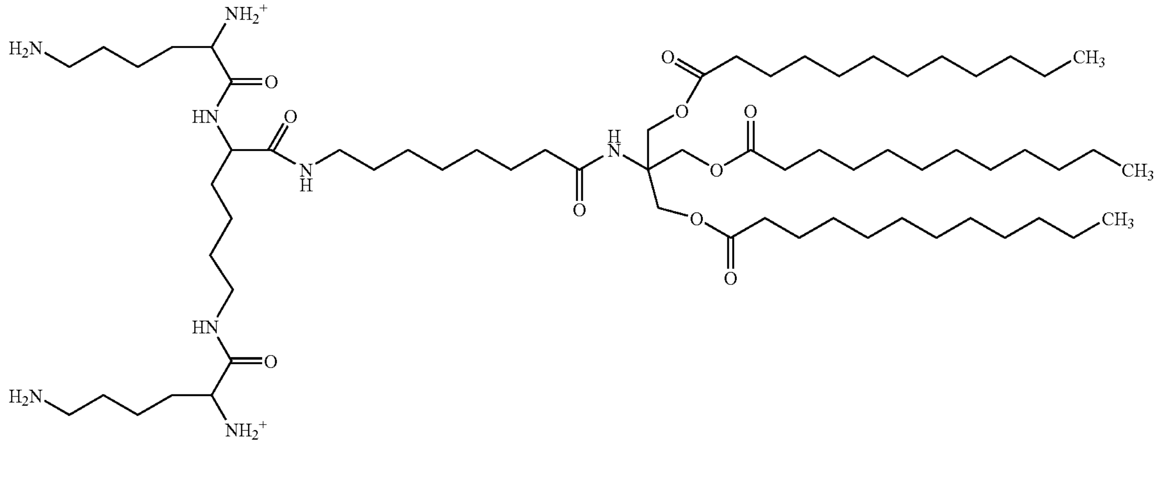

To preserve virus, the concentration of the lipid in the composition is preferably in the range from 0.1 μM to 1 mM. More preferably the concentration of the lipid is 1 μM to 500 μM. In the most preferred embodiment, the concentration of the lipid is 5 μM to 100 μM.

In the case where the lipid in the composition is trilysine-carpryloyl-tris-trilaurate (CS087), the concentration of the lipid is preferably in the range from 10 to 50 μM. Most preferably, the concentration of trilysine-carpryloyl-tris-trilaurate in the composition is 10 μM.

The cryoprotectant in the composition according to the various forms of the present invention is any molecule that has the function of substantially inhibiting the formation of ice crystals upon freezing of a liquid. The cryoprotectant may be a sugar, sugar alcohol, glycerol, amino acid including glycine, histidine or arginine, peptide, polypeptide, protein including albumin and gelatine, or polymer including dextran, polyvinyl pyrrolidone, polyvinyl alcohol or polyethylene glycol, or any combination of such molecules.

The determination of whether a molecule may function as a cryoprotectant may be by a suitable method known in the art in which the function of a molecule to substantially inhibiting the formation of ice crystals upon freezing of a liquid may be tested.

In a preferred embodiment of the invention, the cryprotectant is a poly-hydroxy compound. More preferably, the poly-hydroxy compound is a sugar. More preferably, the sugar is sucrose, trehalose, dextrose, lactose, maltose or glucose. In a particularly preferred embodiment, the cryoprotectant is sucrose.

To preserve virus, the concentration of the cryoprotectant in the composition may be in the range of 0.1 to 20% weight/volume. Preferably, the concentration is in the range of 1 to 10% weight/volume. When the cryoprotectant present in the composition is sucrose, preferably the concentration of sucrose is 8.5%.

It has also been found that the presence of a surfactant in the composition may further improve the ability of the composition to preserve a virus. The surfactant is any molecule that can reduce the interfacial tension between two immiscible phases. Preferably the surfactant is a non-ionic surfactant.

The determination of whether a molecule may function as a surfactant may be by a suitable method known in the art in which the function of a molecule to reduce the interfacial tension between two immiscible phases may be tested.

Preferably, the surfactant is present in the composition at a concentration in the range from 0.0001% to 50% volume/volume. More preferably, the surfactant is present in the composition at a concentration in the range from 0.001% to 10% volume/volume.

In a preferred embodiment, the non-ionic surfactant is a molecule that includes an oxyethylene group and a hydroxy group. Most preferably, the non-ionic surfactant is polysorbate 80 or polyethylene glycol 400, or any combination of these non-ionic surfactants.

When polysorbate 80 is used in the composition, the concentration of the polysorbate 80 is preferably 0.0001 to 1% volume/volume. More preferably, the concentration of polysorbate 80 in the composition is 0.001 to 0.1% volume/ volume. Most preferably, the concentration of polysorbate 80 in the composition is 0.005% volume/volume.

When polyethylene glycol 400 is used in the composition, the concentration is preferably 0.001 to 50% volume/volume. More preferably, the concentration of polyethylene glycol 400 is 0.01 to 10% volume/volume. More preferably, the concentration of polyethylene glycol 400 is 0.01 to 5% volume/volume. Most preferably, the concentration of polyethylene glycol 400 in the composition is 0.5% volume/volume.

The pH of the composition may also be selected to improve viral preservation. The pH may also be selected to be compatible with the administration of the composition to a subject for therapeutic purposes. Preferably, the pH of the composition is in the range of 4 to 10. More preferably, the pH is in the range of to 9. In the most preferred form of the invention, the pH of the composition is in the range of 6 to 8.5.

The pH of the composition according to the various forms of the present invention may be obtained by buffering with a pharmaceutically acceptable buffer. Preferably, the buffer is selected from one or more buffers selected from the group consisting of monobasic acids including acetic, benzoic, gluconic, glyceric and lactic acids, dibasic acids including aconitic, adipic, ascorbic, carbonic, glutamic, maleic, malic, succinic, tartaric acids, polybasic acids including citric and phosphoric acids. The buffer may also be selected from one or more buffers selected from the group consisting of bases including ammonia or ammonium chloride, diethanolamine, glycine, tromethamine (also known as Tris and Tham).

Preferably, the buffer is selected from one or more buffers selected from the group consisting of a tris-based buffer, a sodium hydrogen maleate buffer, succinate buffer, or phosphate buffer. Tris-based buffers and sodium hydrogen maleate buffers are particularly preferred.

The composition according to the present invention provides a composition for the improved preservation of a virus. In one embodiment, the present invention provides a composition for the preservation of a virus, the composition including a virus, a lipid and a cryoprotectant, wherein when the composition is frozen the virus is storage stable.

Preferably, the temperature of storage of the composition is from −200° C. to 0° C. More preferably, the temperature of storage is −100° C. to −5° C. Most preferably, the temperature of storage is −80° C. to −20° C.

With respect to the period of time over which the composition according to the present invention shows improved storage stability, the composition according to the present invention may be stored for a period of greater than 24 months. Preferably the period of storage is 12 months or greater. More preferably, the period of storage is 6 months or greater. More preferably, the period of storage is 3 months or greater. More preferably, the period of storage is 1 week or greater. Most preferably, the period of storage is 1 day or greater.

In this regard, as has been discussed previously, the improved preservation will be as compared to a composition that does not contain lipid, or a composition that does not contain cryoprotectant. That is, the activity of the virus will not decrease substantially with time when the composition is stored at the abovementioned temperatures or for the abovementioned periods of time, as compared to a composition not containing lipid, or a composition not containing a cryoprotectant. The activity of the virus may be a desired activity of the virus in the composition, such as infectivity, ability to transduce or immunogenicity.

The composition according to the present invention also shows improved preservation of a virus when the composition is frozen. The composition also shows improved preservation of a virus when the composition is thawed, or when the composition is subjected to one or more cycles of freezing and thawing. In a preferred embodiment, the present invention provides a composition for the preservation of a virus, the composition including a virus, a lipid and a cryoprotectant, wherein the virus is stable to freeze-thawing.

The improved preservation with regard to freeze-thawing will be as compared to a composition that does not contain lipid. That is, the activity of the virus will not decrease substantially with time when the composition is frozen and thawed, or subjected to multiple cycles of freeze-thawing, as compared to a composition not containing lipid. The activity of the virus may be a desired activity of the virus in the composition, such as infectivity, ability to transduce or immunogenicity.

The composition according to the present invention may also be in a dosage form suitable for administration to a human or an animal subject. The dosage form includes the composition according to the present invention and may further include other pharmaceutically acceptable additives.

The addition of such pharmaceutically acceptable additives to the dosage form may be to improve the ability of the virus to infect or transduce target cells, or to improve the activity elicited by the administration of virus. For example, local bystander killing can be enhanced by co-administration of a pharmaceutical or genetic agent which enhances cell-cell communications. Another example is the co-administration of a DNA encoding a cytokine to increase the immunogenicity of tumour cells. Another example is the inclusion of an adjuvant compound in a vaccine to enhance immune response.

The present invention also provides a method of producing a composition for the preservation of a virus, the method including the step of preparing a liquid composition including a virus, a lipid and a cryoprotectant.

As will be appreciated, the methods according to the present invention will embody the same preferred features as those for the composition as discussed in detail above.

With regard to the preparation of virus, the virus may be purified by any suitable means. Preferably, the virus is purified by a chromatographic method including ion-exchange chromatography or HPLC, or centrifugation including CsCl centrifugation, after the virus has been recovered from infected permissive cells and/or the supernatant thereof. Preferably, the virus is purified by a chromatographic method. When purified by CsCl centrifugation, the virus is prepared after recovery from infected permissive cells by centrifugation through a CsCl step gradient and centrifugation to equilibrium on a CsCl gradient. When virus is purified in this manner, the CsCl is preferably removed by column chromatography.

Preferably, the concentrated virus so formed is diluted in a solution that includes a suitable buffer and a cryoprotectant. More preferably, the solution further includes a non-ionic surfactant. In a preferred embodiment, the concentrated virus is diluted in a solution including a Tris buffer, sucrose and polyethylene glycol 400 and/or polysorbate 80. In a particularly preferred embodiment, the concentrated virus is diluted in a solution (at pH 8.0) including 10 mM Tris buffer, 8.5% sucrose and 2% polyethylene glycol 400. Preferably, the solution (which may exist as a suspension) containing virus is then filtered to remove unwanted micro-organisms. Most preferably, the solution is filtered through a 0.2 micron membrane filter.

For the preparation of a composition according to the present invention, the lipid is preferably first dispersed in a solution identical to that used for the dilution of virus. Preferably, the solution (which may exist as a suspension) containing lipid is filtered to remove unwanted micro-organisms. Most preferably, the solution is filtered through a 0.2 micron membrane filter.

To prepare a composition for the preservation of virus, the diluted solution of virus (which may exist as a suspension) may then be combined with a solution containing lipid (which may also exist as a suspension), the relative proportions of each selected so as to achieve the desired final concentrations of virus and lipid. Accordingly, the method according to the present invention provides a method for producing a composition for the preservation of a virus, wherein the composition is formed by combining a solution including a virus and a cryoprotectant with a solution including lipid.

The composition so formed may be stored in a suitable closed container. Preferably the composition is stored in borosilicate glass vials. In addition, the composition may be stored under a suitable gas or mixture of gases.

DESCRIPTION OF THE PREFERRED EMBODIMENTS

Reference will now be made to examples that embody the above general principles of the present invention. However, it is to be understood that the following description is not to limit the generality of the above description.

EXAMPLE 1

Preparation of a Composition for the Preservation of Virus

CsCl purified OAdV623 virus was suspended in a pH 8.0 buffer containing 10 mM Tris, 8.5% sucrose, 2% PEG buffer, in a polypropylene tube, at two-times the final concentration. CS087 was supplied as a freeze-dried solid that was first dissolved in ethanol and the ethanol then removed to produce a film. The film was dispersed in a pH 8.0 buffer containing 10 mM Tris, 8.5% sucrose, 2% polyethylene glycol 400, in a polystyrene tube, at two-times the final concentration.

The suspensions of OAdV623 and CS087 were filtered separately through a 0.2 μm membrane filter. An equal volume of OAdV623 and CS087 were combined aseptically. The suspension was then gently agitated continuously at approximately 40 rpm for 60 to 90 minutes at 18° C.–20° C., to ensure viral mixing. The final product was then aseptically dispensed into washed and autoclaved Type I borosilicate glass vials and stored at the appropriate temperature.

EXAMPLE 2

Storage Stability of Various Viral Compositions at −80° C.

The stability of various OAdV623 compositions (approximately $6\times10^8$ VP/ml) stored at −80° C. was assessed by determining the extent of cell killing after storage for 14 days, 1 month or 3 months. Cell killing was determined for compositions stored at pH 8 and pH 6.

OAdV623 encodes the PNP gene which catalyses the conversion of the immunosuppressive prodrug Fludarabine to the toxic 2-fluoro-adenine product. This results in the death of cells producing PNP and to a limited extent, cells in the vicinity with a near neighbour bystander effect. The death of susceptible cells, such as the PC3 cell line, following transduction with OAdV623 and treatment with Fludarabine phosphate, is a direct indicator of the potency of the OAdV623 preparation.

To determine the extent of cell killing, an aliquot of virus in the relevant composition was thawed and approximately $6\times10^6$ virus particles were used to transduce $1\times10^4$ PC3 cells in culture. The ability of the virus to kill PC3 cells by converting the prodrug fludarabine, supplied to the cells as fludarabine phosphate, to active 2-fluoroadenine, was then determined quantitatively. Cell killing was determined by an MTS assay (Promega) to measure the number of viable cells in treated wells compared to a standard curve of cells not treated with the virus.

The concentration of the various components used was as follows:

10 mM Tris
10 mM sodium hydrogen maleate
8.5% sucrose
50 μM CS087
2% (v/v) polyethylene glycol 400 (PEG400)
0.005% (v/v) polysorbate 80 (PS80)

The whole composition was buffered to the desired pH with Tris or maleate buffer.

(a) Stability at pH 8 is shown in FIG. 1.

| | % Cell Killing | | |
|---|---|---|---|
| Composition | 14 days | 1 month | 3 months |
| Tris/sucrose | 41.4 ± 13.9 | −13.3 ± 30.3 | −14.2 ± 16.0 |
| Tris/sucrose/CS087 | 34.6 ± 19.3 | 52.6 ± 14.6 | 0.1 ± 11.0 |
| Tris/sucrose/CS087/PEG400 | 62.1 ± 1.3 | 68.9 ± 7.9 | 53.5 ± 5.0 |
| Tris/sucrose/CS087/PS80 | 63.3 ± 0.7 | 74.2 ± 0.8 | 48.2 ± 4.9 |
| Tris/sucrose/PEG400 | 52.8 ± 1.5 | 3.0 ± 40.2 | 4.0 ± 4.4 |
| Tris/sucrose/PS80 | 40.3 ± 7.3 | 15.1 ± 9.3 | 5.3 ± 17.4 |

As can be seen, OAdV623 stored in tris/sucrose at −80° C. was stable for 2 weeks only. The addition of lipid to the tris/sucrose composition enhanced the preservation of the virus, when the virus was stored at −80° C. for periods of at least 1 month and then subsequently thawed. The addition of a non-ionic surfactant to the tris/sucrose/lipid composition further enhanced the preservation of virus, such that the virus remained active even after a storage period of 3 months and a subsequent freeze-thaw cycle. Thus the preservation of the virus after storage and subsequent thawing was improved by the addition of lipid and, in particular, lipid plus a non-ionic surfactant.

Figure 2:
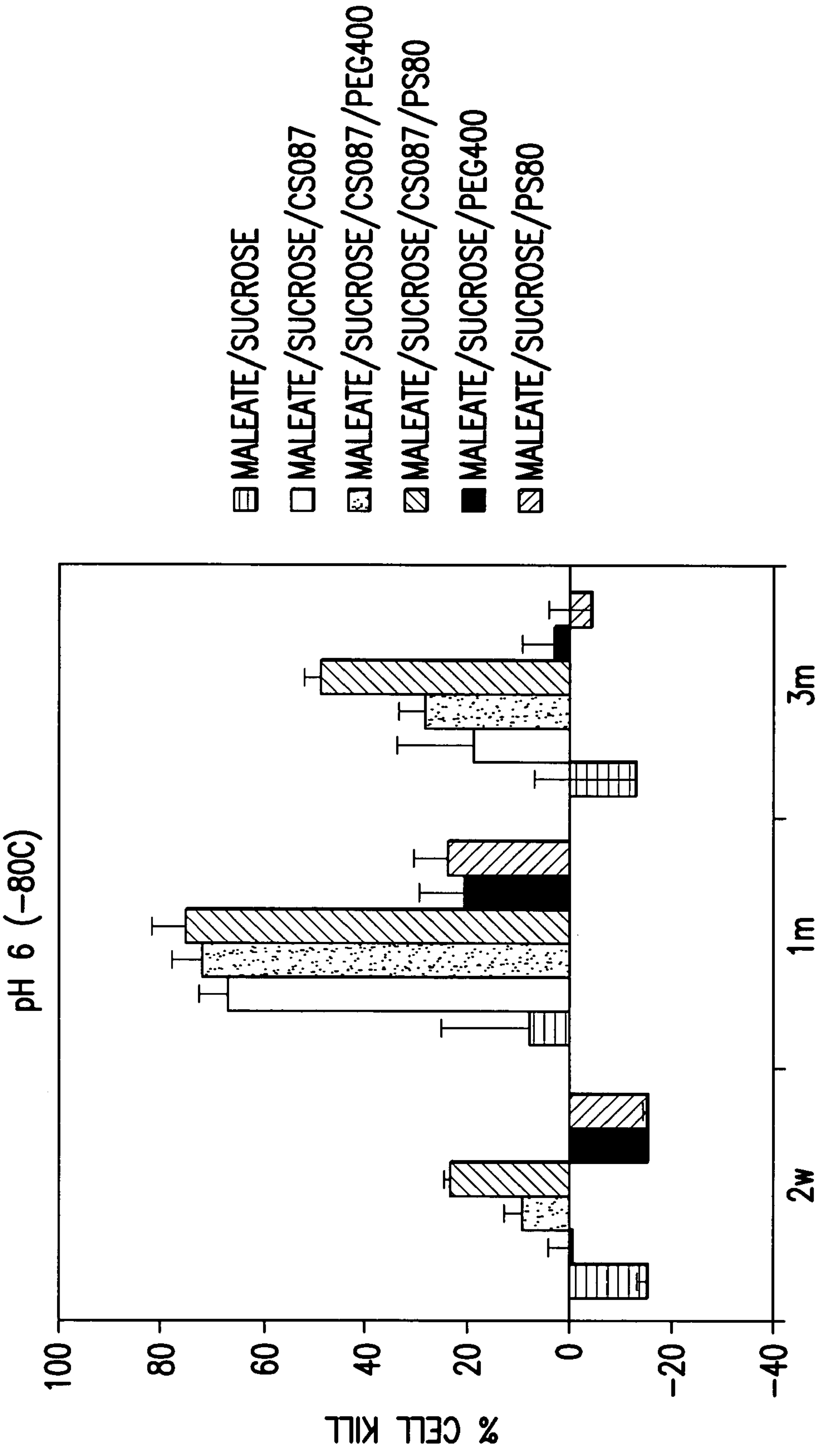
FIG. 2: shows the storage stability of various viral compositions at pH6 and −80° C.

(b) Stability at pH 6 is shown in FIG. 2.

| | % Cell Killing | | |
|---|---|---|---|
| Composition | 14 days | 1 month | 3 months |
| Maleate/sucrose | −15.4 ± 1.8 | 7.9 ± 16.9 | −12.8 ± 19.8 |
| Maleate/sucrose/CS087 | −0.2 ± 4.1 | 66.8 ± 5.7 | 18.9 ± 15.2 |
| Maleate/sucrose/CS087/PEG400 | 9.1 ± 3.5 | 71.7 ± 6.2 | 28.5 ± 4.6 |
| Maleate/sucrose/CS087/PS80 | 23.4 ± 1.1 | 75.2 ± 6.5 | 48.6 ± 3.5 |
| Maleate/sucrose/PEG400 | −15.2 ± 1.8 | 20.9 ± 8.7 | 2.7 ± 6.3 |
| Maleate/sucrose/PS80 | −15.4 ± 1.0 | 24.1 ± 6.5 | −4.0 ± 7.9 |

As can be seen, the addition of lipid to the tris/sucrose composition enhanced the preservation of the virus, when the virus was stored at −80° C. such that the virus remained active after a storage period of 3 months and a subsequent freeze-thaw cycle. The addition of a non-ionic surfactant to the tris/sucrose/lipid composition further enhanced the preservation of virus. Thus the preservation of the virus after storage and subsequent thawing was improved by the addition of lipid and, in particular, lipid plus a non-ionic surfactant.

EXAMPLE 3

Storage Stability of Various Viral Compositions at −20° C.

The stability of various OAdV623 compositions (approximately $6\times10^8$ VP/ml) stored at −20° C. was assessed by determining the extent of cell killing after storage for 14 days, 1 month or 3 months. Cell killing was determined for formulations stored at pH 8 and pH 6.

To determine the extent of cell killing, an aliquot of virus in the relevant composition was thawed and approximately $6\times10^6$ virus particles were used to transduce $1\times10^4$ PC3 cells in culture. The ability of the virus to kill PC3 cells by converting the prodrug fludarabine, supplied to the cells as fludarabine phosphate, to active 2-fluoroadenine, was then determined quantitatively. Cell killing was determined by an MTS assay (Promega) to measure the number of viable cells in treated wells compared to a standard curve of cells not treated with the virus.

The concentration of the various components used was as follows:

10 mM Tris 10 mM sodium hydrogen maleate 8.5% sucrose

50 μM CS087

2% (v/v) polyethylene glycol 400 (PEG400)

0.005% (v/v) polysorbate 80 (PS80)

The whole composition was buffered to the desired pH with Tris or maleate buffer.

Figure 3:
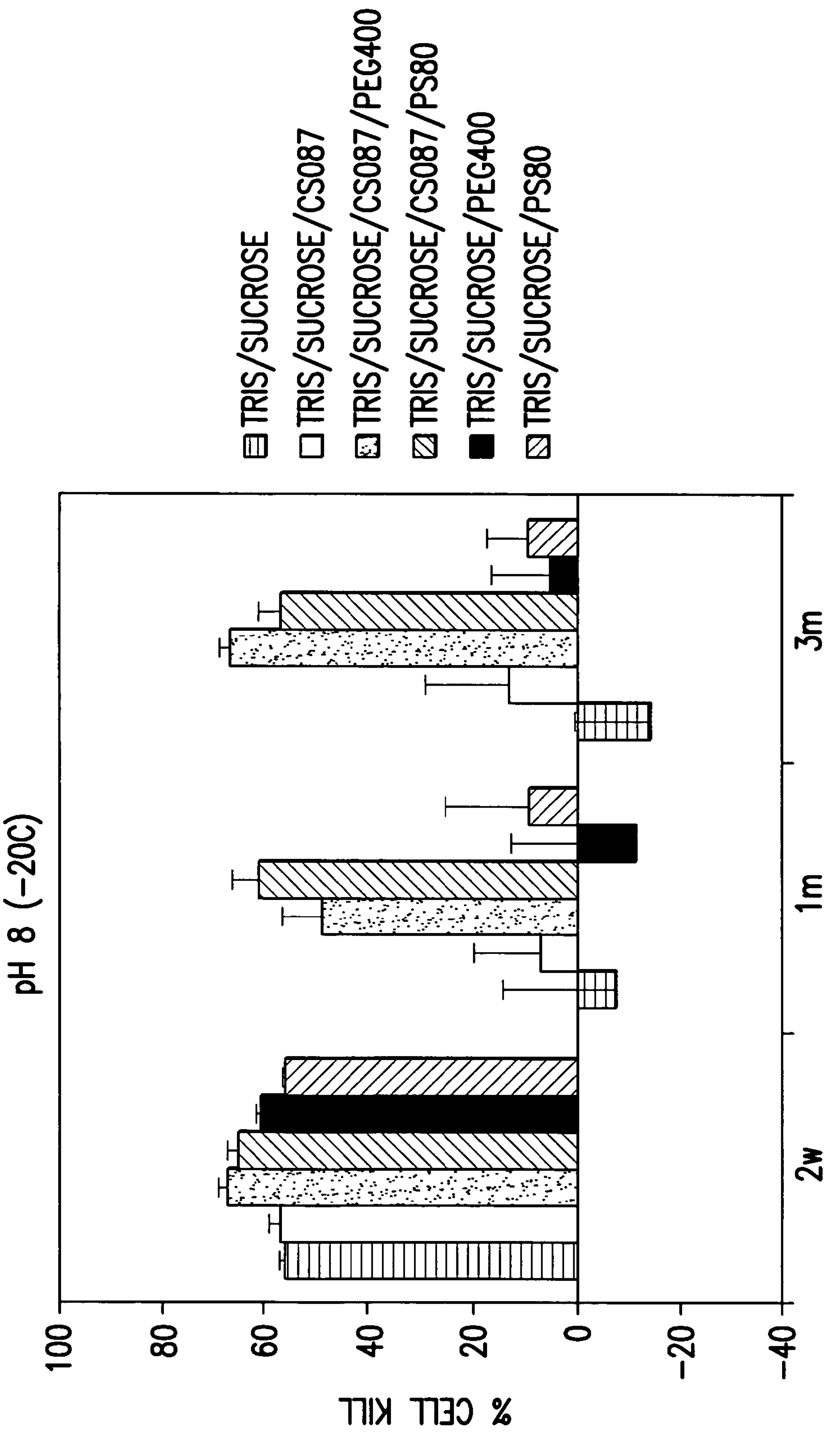
FIG. 3: shows the storage stability of various viral compositions at pH8 and −20° C.

(a) Stability at pH 8 is shown in FIG. 3.

| | % Cell Killing | | |
|---|---|---|---|
| Composition | 14 days | 1 month | 3 months |
| Tris/sucrose | 56.0 ± 1.3 | −7.6 ± 21.7 | −14.2 ± 14.7 |
| Tris/sucrose/CS087 | 57.3 ± 1.8 | 6.9 ± 12.9 | 13.5 ± 15.5 |
| Tris/sucrose/CS087/PEG400 | 67.2 ± 1.6 | 49.0 ± 7.5 | 66.8 ± 2.1 |
| Tris/sucrose/CS087/PS80 | 65.5 ± 1.9 | 61.2 ± 5.0 | 57.2 ± 4.2 |
| Tris/sucrose/PEG400 | 60.5 ± 1.1 | −11.2 ± 24.0 | 4.8 ± 11.7 |
| Tris/sucrose/PS80 | 55.9 ± 0.6 | 9.2 ± 15.8 | 9.4 ± 8.1 |

As can be seen, the addition of lipid to the tris/sucrose composition enhanced the preservation of the virus, when the virus was stored at −20° C. such that the virus remained active after a storage period of 3 months and a subsequent freeze-thaw cycle. The addition of a non-ionic surfactant to the tris/sucrose/lipid composition further enhanced the preservation of virus, such that greater activity (% cell kill) was observed compared to the tris/sucrose/lipid composition without a non-ionic surfactant. Thus the preservation of the virus after storage and subsequent thawing was improved by the addition of lipid and, in particular, lipid plus a non-ionic surfactant.

Figure 4:
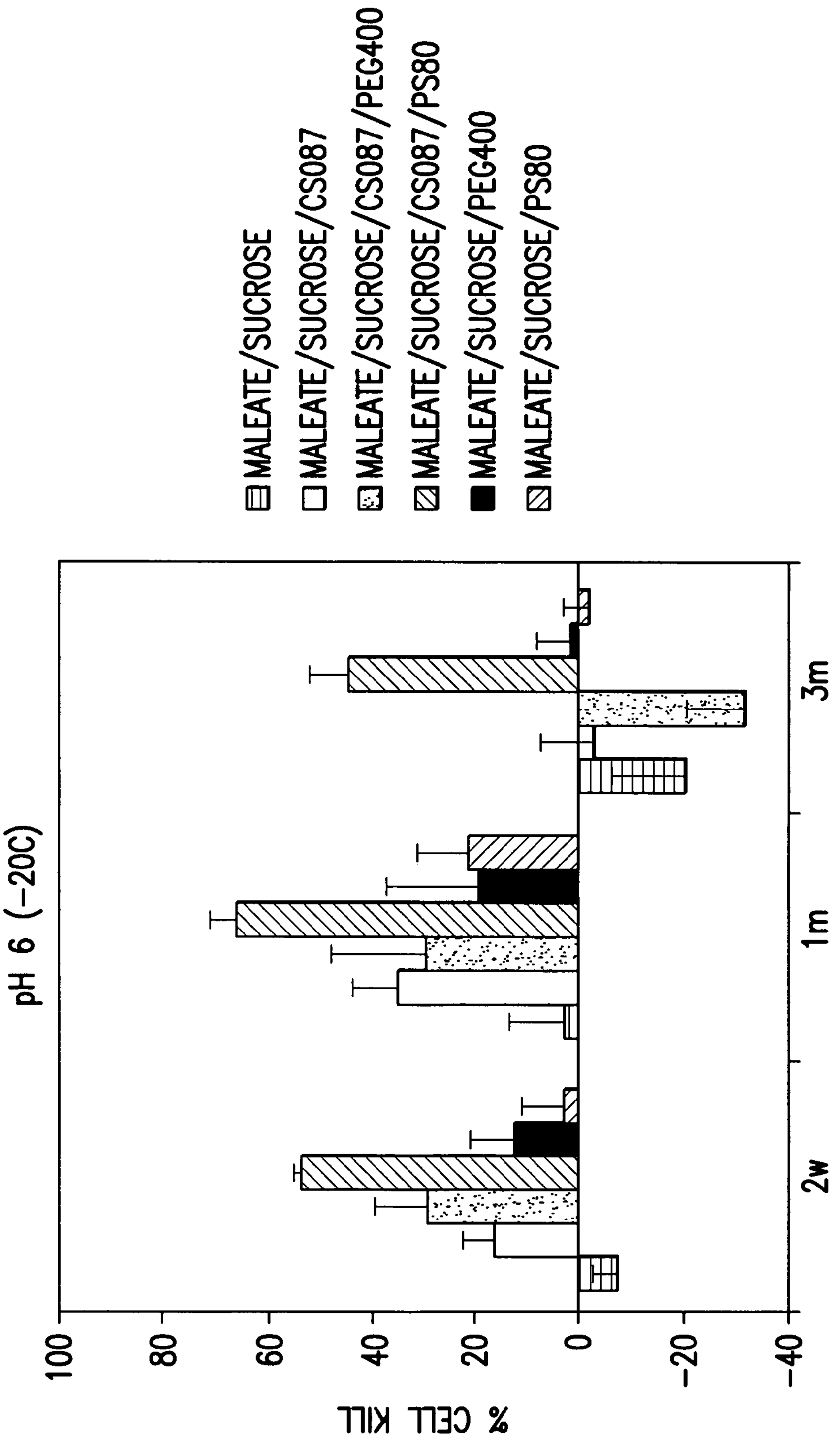
FIG. 4: shows the storage stability of various viral compositions at pH6 and −20° C.

(b) Stability at pH 6 is shown in FIG. 4.

| | % Cell Killing | | |
|---|---|---|---|
| Composition | 14 days | 1 month | 3 months |
| Maleate/sucrose | −7.1 ± 4.8 | 3.0 ± 10.8 | −20.2 ± 14.2 |
| Maleate/sucrose/CS087 | 16.4 ± 5.7 | 35.0 ± 8.7 | −2.6 ± 10.2 |
| Maleate/sucrose/CS087/PEG400 | 29.4 ± 10.0 | 29.9 ± 18.0 | −31.3 ± 10.8 |
| Maleate/sucrose/CS087/PS80 | 53.6 ± 1.5 | 66.1 ± 5.2 | 44.7 ± 7.6 |
| Maleate/sucrose/PEG400 | 12.4 ± 8.7 | 19.7 ± 17.7 | 1.9 ± 6.1 |
| Maleate/sucrose/PS80 | 3.1 ± 8.1 | 21.6 ± 9.7 | −1.1 ± 4.6 |

The addition of lipid to the tris/sucrose composition enhanced the preservation of the virus, when the virus was stored at −20° C. such that the virus remained active after a storage period of 1 month and a subsequent freeze-thaw cycle. The addition of a non-ionic surfactant to the tris/sucrose/lipid composition further enhanced the preservation of virus. Thus the preservation of the virus after storage and subsequent thawing was improved by the addition of lipid and, in particular, lipid plus a non-ionic surfactant.

EXAMPLE 4

Preservation of Various Viral Compositions Upon Multiple Freeze-Thaw Cycles (−80° C. to 25° C.)

The ability of various OAdV623 compositions ($1\times10^{10}$ VP/ml) to be preserved after multiple freeze-thaw cycles was assessed by determining the extent of cell killing after exposure to 1, 2 or 3 freeze-thaw cycles. For each cycle, virus was frozen at −80° C. for no less than 1 hour and thawed at 25° C. for 30 minutes. Cell killing was determined for virus formulated in 10 mM Tris, 8.5% sucrose, 50 μM CS087 and either 2% or 4% polyethylene glycol 400 (pH 8).

To determine the extent of cell killing, virus particles in the range of $4\times10^5$ to $3\times10^7$ were used to transduce $1\times10^4$ PC3 cells in culture. The ability of the virus to kill PC3 cells by converting the prodrug fludarabine, supplied to the cells as fludarabine phosphate, to active 2-fluoroadenine, was then determined quantitatively. Cell killing was determined by an MTS assay (Promega) to measure the number of viable cells in treated wells compared to a standard curve of cells not treated with the virus.

The concentration of the various components used was as follows:

10 mM Tris 8.5% sucrose

50 μM CS087

2% or 4% (v/v) polyethylene glycol 400 (PEG400)

The whole composition was buffered to the desired pH with Tris or maleate buffer.

Figure 5:
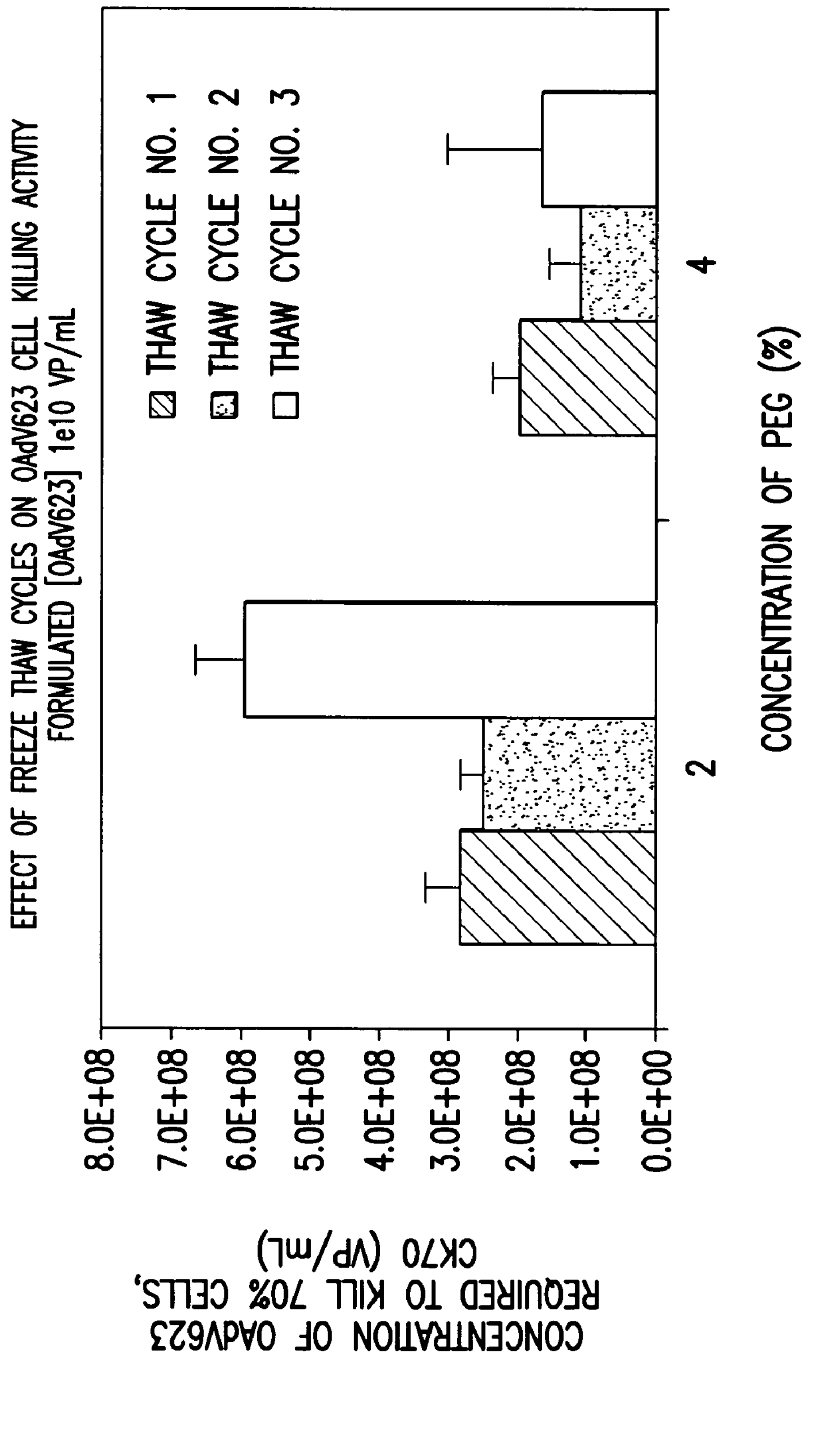
FIG. 5: shows the effect of multiple freeze-thaw cycles on various viral compositions.

The results are as shown in FIG. 5.

As can be seen, the composition containing either 2% or 4% polyethylene glycol 400 provides substantial protection to the virus against the effects of freeze-thawing of the composition. In particular, protection against the effect of repeated freeze-thawing is most significant for the composition containing 4% polyethylene glycol.

EXAMPLE 5

Preservation of Various Viral Compositions Upon Multiple Freeze-Thaw Cycles (−80° C. to 20° C.)

The ability of various OAdV623 compositions (approximately $9.6\times10^{11}$ VP/ml) to be preserved after multiple freeze-thaw cycles was assessed by determining the extent of cell killing after exposure to 1 or 3 freeze-thaw cycles. For each cycle, virus was frozen at −80° C. for at least 1 hour and thawed at 20° C. for 40 minutes. Cell killing was determined for virus formulated at pH 8 in 10 mM Tris, 8.5% sucrose and 0.5% polyethylene glycol 400 with or without 10 μM CS087.

To determine the extent of cell killing, virus particles in the range of $8\times10^5$ to $1\times10^8$ were used to transduce $5\times10^3$ PC3 cells in culture. The ability of the virus to kill PC3 cells by converting the prodrug fludarabine, supplied to the cells as fludarabine phosphate, to active 2-fluoroadenine, was then determined quantitatively. Cell killing was determined by an MTS assay (Promega) to measure the number of viable cells in treated wells compared to control cells not treated with the virus.

The concentration of the various components used was as follows:

10 mM Tris
8.5% sucrose
10 μM CS087

0.5% (v/v) polyethylene glycol 400 (PEG400)

The whole composition was buffered to the desired pH with Tris or maleate buffer.

The invention claimed is:

1. A composition for the preservation of a virus, said composition comprising a virus, a polycationic lipid that has a hydrophilic moiety that includes two or more groups derived from positively charged amino acids, and a cryoprotectant, wherein the polycationic lipid has the following chemical formula:

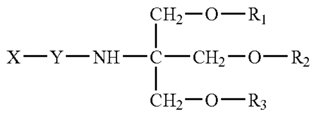

or a salt thereof, wherein X is a positively-charged hydrophilic moiety; Y is a spacer having a carbon chain length equivalent to 1 to 30 carbon-carbon single covalent bonds or is absent; and $R_1$, $R_2$, and $R_3$ are the same or different acyl groups of a fatty acid.

2. A composition according to claim 1, wherein the lipid has the following chemical formula:

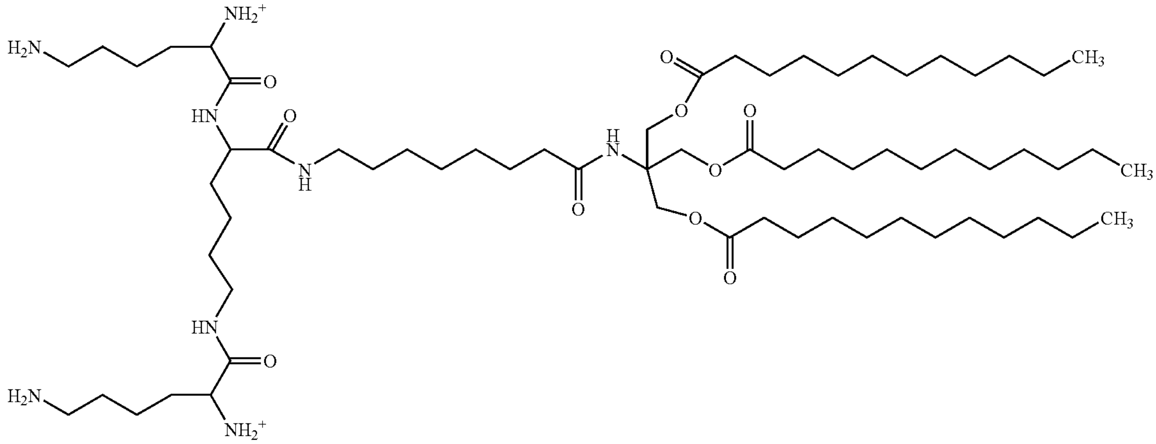

Figure 6:
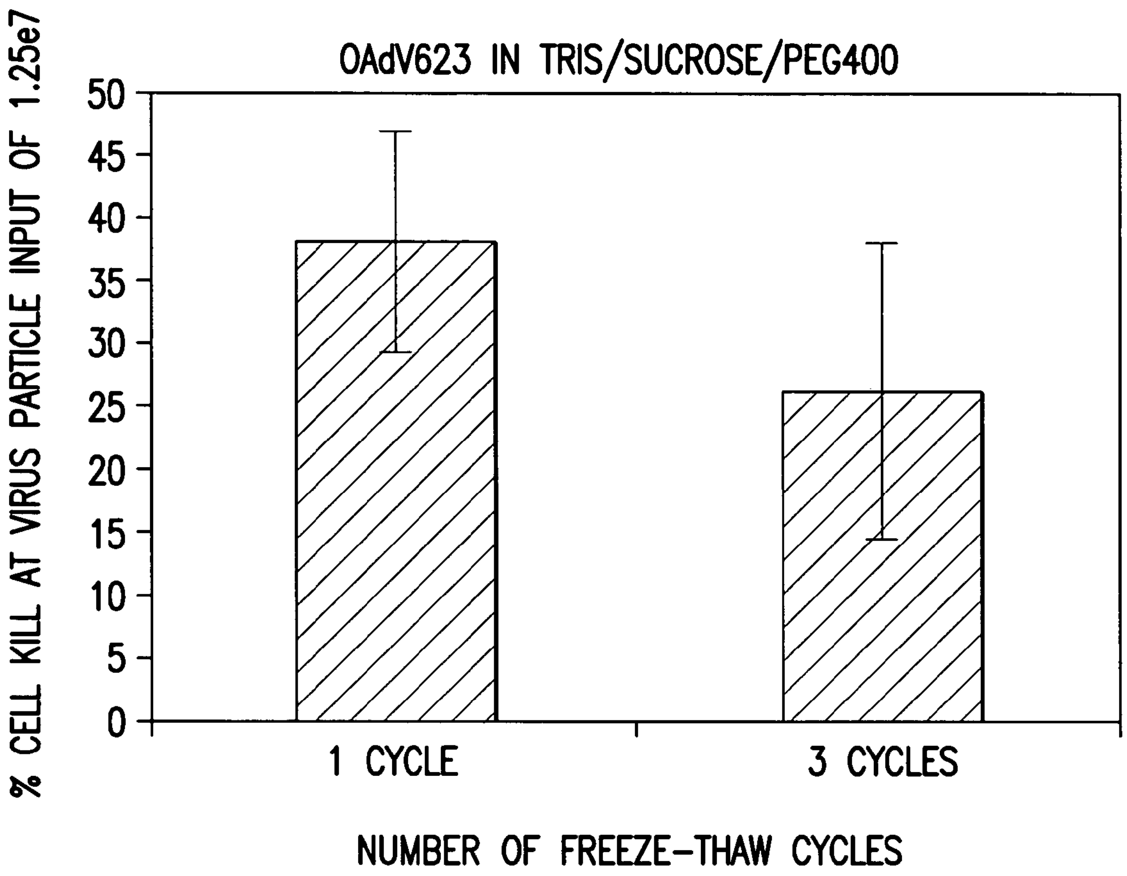
FIG. 6: shows the effects of multiple freeze-thaw cycles on OAdV623 in tris/sucrose/PEG400.
Figure 7:
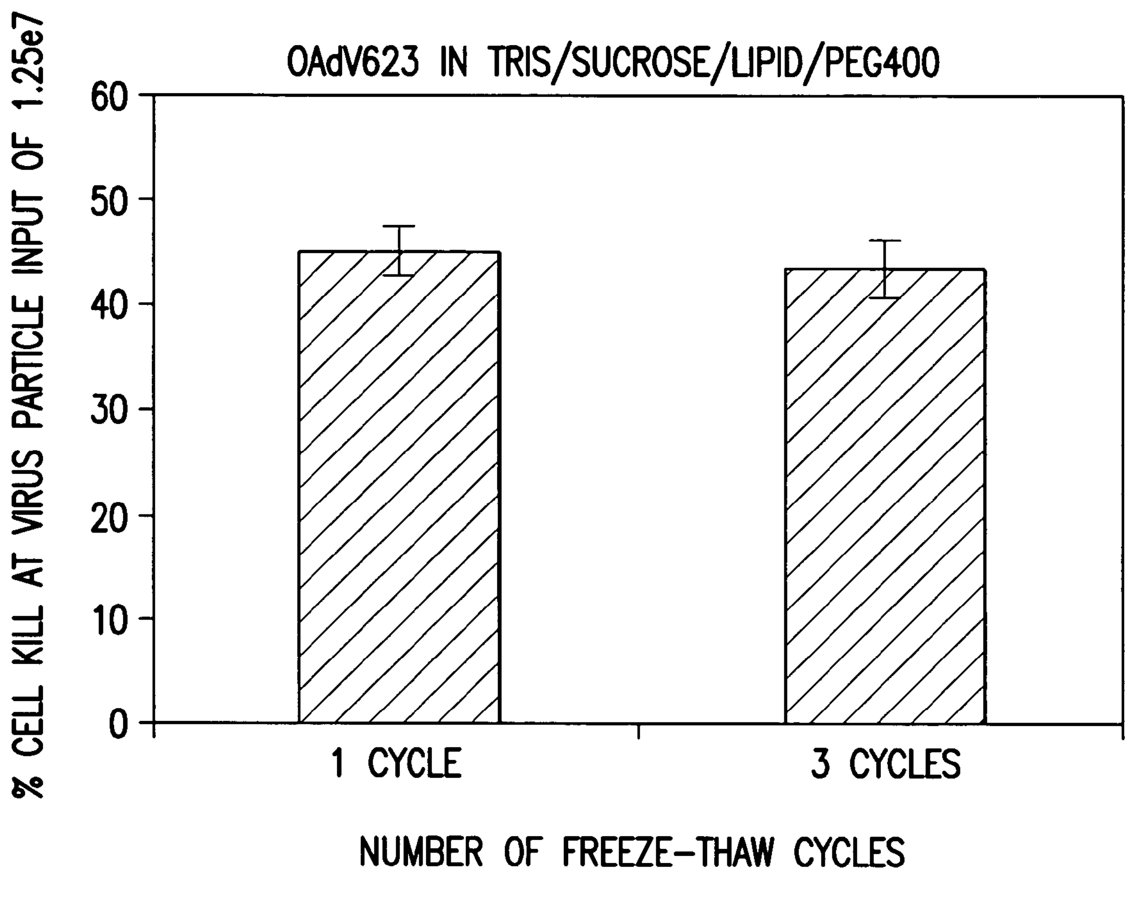
FIG. 7: shows the effects of multiple freeze-thaw cycles on OAdV623 in tris/sucrose/lipid/PEG400.

The results for OAdV623 in tris/sucrose/PEG400 is shown in FIG. 6 and OAdV623 in tris/sucrose/lipid/PEG400 is shown in FIG. 7.

As can be seen, the composition containing 10 μM lipid provides substantial protection to the virus against the effects of repeated freeze-thawing compared to the composition containing tris/sucrose/PEG400 without any lipid.

Finally, it will be appreciated that various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are apparent to those skilled in the field of virology, molecular biology, cryobiology or related fields are intended to be within the scope of the present invention.

3. A composition according to claim 1, wherein the concentration of lipid is in the range from 0.1 μM to 1 mM.

4. A composition according to claim 1, wherein the concentration of lipid is in the range from 1 μM to 500 μM.

5. A composition according to claim 1, wherein the concentration of lipid is in the range from 5 μM to 100 μM.

6. A composition according to claim 2, wherein the concentration of lipid is 10 μM.

7. A composition according to claim 1, wherein the cryoprotectant is a poly-hydroxy compound.

8. A composition according to claim 7, wherein the poly-hydroxy compound is a sugar.

9. A composition according to claim 8, wherein the sugar is sucrose, trehalose, dextrose, lactose, maltose, glucose or any combination of these sugars.

10. A composition according to claim 9, wherein the sugar is sucrose.

11. A composition according to claim 1, wherein the concentration of the cryoprotectant is in the range from 0.1 to 20% weight/volume.

12. A composition according to claim 1, wherein the concentration of the cryoprotectant is in the range from 1 to 10% weight/volume.

13. A composition according to claim 10, wherein the concentration of sucrose is 8.5% weight/volume.

14. A composition according to claim 1, wherein the composition further includes a surfactant.

15. A composition according to claim 14, wherein the surfactant is a non-ionic surfactant.

16. A composition according to claim 15, wherein the non-ionic surfactant is a molecule that includes an oxyethylene group and a hydroxy group.

17. A composition according to claim 16, wherein the non-ionic surfactant is polysorbate 80 or polyethylene glycol 400.

18. A composition according to claim 14, wherein the concentration of the surfactant is in the range from 0.0001% to 10% volume/volume.

19. A composition according to claim 17, wherein the concentration of polysorbate 80 is in the range from 0.0001% to 1% volume/volume.

20. A composition according to claim 17, wherein the concentration of polysorbate 80 is 0.005% volume/volume.

21. A composition according to claim 17, wherein the concentration of polyethylene glycol 400 is in the range from 0.01% to 10% volume/volume.

22. A composition according to claim 17, wherein the concentration of polyethylene glycol 400 is 0.5% volume/volume.

23. A composition according to claim 1, wherein the virus is a virus derived from one or more of the group consisting of Adenoviridae, Herpesviridae, Poxviridae, Papovaviridae, Orthohepadnavirus, Parvoviridae, Birnaviridae, Reoviridae, Flaviviridae, Picornaviridae, Togaviridae, Filoviridae, Paramyxoviridae, Rhabdoviridae, Arenaviridae, Bunyaviridae, Orthomyxoviridae, and Retroviridae.

24. A composition according to claim 23, wherein the virus is derived from the Adenoviridae family of viruses.

25. A composition according to claim 24, wherein the virus is an ovine atadenovirus.

26. A composition according to claim 25, wherein the virus is OAdV623 or a derivative of OAdV623.

27. A composition according to claim 1, wherein the concentration of virus in the composition is in the range from $1\times10^6$ to $1\times10^{14}$ virus particles/ml.

28. A composition according to claim 1, wherein the concentration of virus in the composition is in the range from $1\times10^8$ to $5\times10^{12}$ virus particles/ml.

29. A composition according to claim 1, wherein the pH of the composition is in the range from 4 to 10.

30. A composition according to claim 1, wherein the pH of the composition is in the range from 6 to 8.5.

31. A composition according to claim 1, wherein the virus is storage stable.

32. A composition according to claim 31, wherein the composition is stored at −200° C. to 0° C.

33. A composition according to claim 31, wherein the composition is stored at −80° C. to −20° C.

34. A composition according to claim 31, wherein the composition is stored for 12 months or greater.

35. A composition according to claim 31, wherein the composition is stored for 3 months or greater.

36. A composition according claim 31, wherein the composition is stored for 1 week or greater.

37. A composition according to claim 31, wherein the composition is stored for 1 day or greater.

38. A composition according claim 1, wherein the virus is stable to freeze-thawing.

39. A method of producing a composition for the preservation of a virus, said method comprising preparing a liquid composition comprising a virus, a polycationic lipid that has a hydrophilic moiety that includes two or more groups derived from positively charged amino acids, and a cryoprotectant, wherein the polycationic lipid has the following chemical formula:

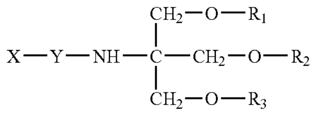

or a salt thereof, wherein X is a positively-charged hydrophilic moiety; Y is a spacer having a carbon chain length equivalent to 1 to 30 carbon-carbon single covalent bonds or is absent; and $R_1$, $R_2$, and $R_3$ are the same or different acyl groups of a fatty acid.

40. A method according to claim 39, wherein the lipid has the following chemical formula:

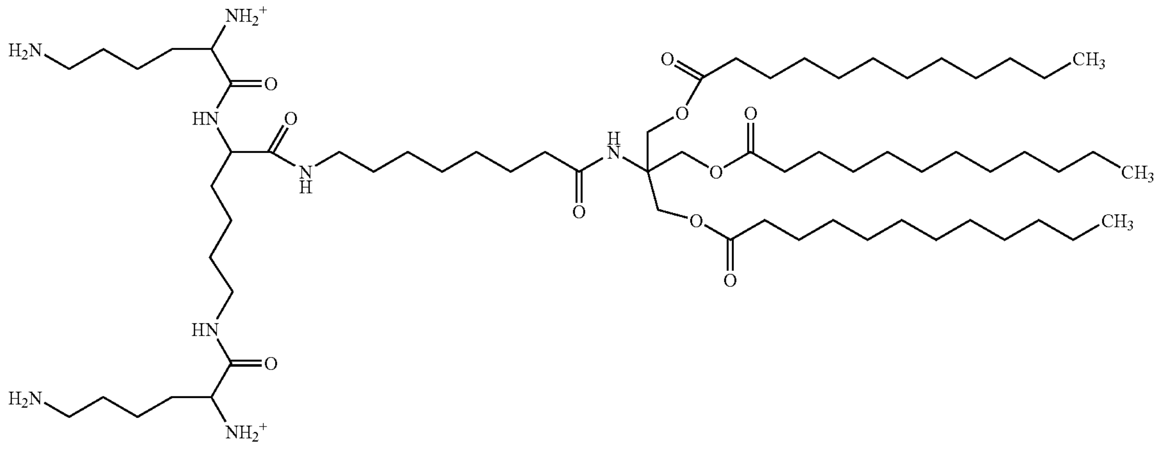

41. A method according to claim 39, wherein the cryoprotectant is a poly-hydroxy compound.

42. A method according to claim 41, wherein the polyhydroxy compound is a sugar.

43. A method according to claim 42, wherein the sugar is sucrose, trehalose, dextrose, lactose, maltose, glucose or any combination of these sugars.

44. A method according to claim 39, wherein the composition further includes a surfactant.

45. A method according to claim 44, wherein the surfactant is a non-ionic surfactant.

46. A method according to claim 45, wherein the nonionic surfactant is a molecule that includes an oxyethylene group and a hydroxy group.

47. A method according to claim 46, wherein the nonionic surfactant is polysorbate 80 or polyethylene glycol 400.

48. A method according to claim 39, wherein the virus is a virus derived from one or more of the group consisting of Adenoviridae, Atadenoviridae, Herpesviridae, Poxviridae, Parvoviridae, Papoviridae, Orthohepadnavirus, Parvoviridae, Birnaviridae, Reoviridae, Flaviviridae, Picornaviridae, Togaviridae, Filoviridae, Paramyxoviridae, Rhabdoviridae, Arenaviridae, Bunyaviridae, Orthomyxoviridae, and Retroviridae.

49. A method according to claim 48, wherein the virus is derived from the Adenoviridae family of viruses.

50. A method according to claim 39, wherein the virus is purified by a method including chromatography or centrifugation.

51. A method according to claim 39, wherein the composition is formed by combining a solution including the virus and the cryoprotectant with a solution including the lipid.

52. A method according to claim 39, wherein the virus is storage stable.

53. A method according to claim 39, wherein the virus is stable to freeze-thawing.

54. A composition for the preservation of a virus, said composition comprising a virus, a polycationic lipid that has a hydrophilic moiety that includes two or more groups derived from positively charged amino acids, and a cryoprotectant, wherein the virus is storage stable when the composition is stored as a frozen liquid, and wherein the polycationic lipid has the following chemical formula:

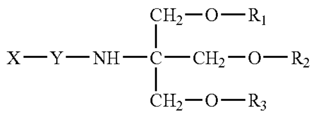

or a salt thereof, wherein X is a positively-charged hydrophilic moiety; Y is a spacer having a carbon chain length equivalent to 1 to 30 carbon-carbon single covalent bonds or is absent; and $R_1$, $R_2$, and $R_3$ are the same or different acyl groups of a fatty acid.

55. A composition for the preservation of a virus, said composition comprising a virus, a polycationic lipid that has a hydrophilic moiety that includes two or more groups derived from positively charged amino acids, and a cryoprotectant, wherein the virus is stable to freeze-thawing, and wherein the polycationic lipid has the following chemical formula:

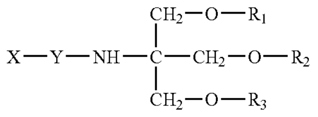

or a salt thereof, wherein X is a positively-charged hydrophilic moiety; Y is a spacer having a carbon chain length equivalent to 1 to 30 carbon-carbon single covalent bonds or is absent; and $R_1$, $R_2$, and $R_3$ are the same or different acyl groups of a fatty acid.

* * * * *